United States Patent
Dey et al.

(10) Patent No.: US 12,118,468 B2
(45) Date of Patent: *Oct. 15, 2024

(54) METHODS AND SYSTEMS FOR PREDICTING PRESCRIPTION DIRECTIONS USING MACHINE LEARNING ALGORITHM

(71) Applicant: Express Scripts Strategic Development, Inc., St. Louis, MO (US)

(72) Inventors: Sudipto Dey, Parsippany, NJ (US); Pulla Reddy P. Yeduru, Leander, TX (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,098

(22) Filed: Sep. 5, 2023

(65) Prior Publication Data
US 2023/0409905 A1 Dec. 21, 2023

Related U.S. Application Data

(63) Continuation of application No. 17/939,060, filed on Sep. 7, 2022, now Pat. No. 11,783,186, which is a
(Continued)

(51) Int. Cl.
*G06N 20/00* (2019.01)
*G06N 3/08* (2023.01)
(Continued)

(52) U.S. Cl.
CPC .............. *G06N 3/08* (2013.01); *G06N 20/00* (2019.01); *G06Q 40/08* (2013.01); *G16H 20/10* (2018.01); *G06N 3/045* (2023.01)

(58) Field of Classification Search
CPC ................. G06N 3/08; G06N 20/00
See application file for complete search history.

(56) References Cited

U.S. PATENT DOCUMENTS 11,929,155 B1 * 3/2024 Schoenberg .......... H04L 63/105
2011/0202486 A1 8/2011 Fung
(Continued)

OTHER PUBLICATIONS

Google AI Blog; Moving Beyond Translation with the Universal Transformer; https://ai.googleblog.com/2018/08/moving-beyond-translation-with.html; Aug. 15, 2018.
(Continued)

*Primary Examiner* — Michael T Vu
(74) *Attorney, Agent, or Firm* — Husch Blackwell LLP

(57) ABSTRACT

Methods and systems for predicting prescription drug directions are described. In one embodiment, a drug direction prediction subsystem receives and pre-processes values of a plurality of required pharmacy elements for a corresponding prescription of a plurality of prescriptions, generates respective weights for the values of the plurality of required pharmacy elements of the prescription based on one or more of the values of the plurality required pharmacy elements of the prescription, creates a machine learning model to be used by the applicable one of the plurality of machine learning algorithms in predicting drug directions of the prescription, the machine learning model using the values of the plurality of required pharmacy elements of the prescription and the respective weights, and predicts a plurality of drug directions of a new prescription by executing the machine learning model using weighted values of the plurality of required pharmacy elements of the new prescription.

20 Claims, 7 Drawing Sheets

Related U.S. Application Data continuation of application No. 16/527,613, filed on Jul. 31, 2019, now Pat. No. 11,468,320.

(51) Int. Cl.
  *G06Q 40/08* (2012.01)
  *G16H 20/10* (2018.01)
  *G06N 3/045* (2023.01)

(56) References Cited

U.S. PATENT DOCUMENTS

| | | |
|---|---|---|
| 2014/0278507 A1 | 9/2014 | Potter |
| 2015/0142479 A1 | 5/2015 | Porter |
| 2015/0356252 A1 | 12/2015 | Beker |
| 2016/0092652 A1 | 3/2016 | Stewart |
| 2016/0267224 A1 | 9/2016 | Natarajan |
| 2016/0328526 A1 | 11/2016 | Park |
| 2017/0046491 A1 | 2/2017 | Scantland |
| 2018/0075220 A1 | 3/2018 | Hill, Sr. |
| 2018/0276694 A1 | 9/2018 | Ross |
| 2019/0080416 A1 | 3/2019 | Smith |
| 2019/0156257 A1 | 5/2019 | Datta Ray |
| 2019/0244701 A1 | 8/2019 | Swenson |
| 2020/0012124 A1 | 1/2020 | Waite |

OTHER PUBLICATIONS

Wu, Yonghui, et al. "Google's neural machine translation system: Bridging the gap between human and machine translation." https://arxiv.org/abs/1609.08144, 2016.

* cited by examiner

METHODS AND SYSTEMS FOR PREDICTING PRESCRIPTION DIRECTIONS USING MACHINE LEARNING ALGORITHM

CROSS REFERENCE TO RELATED APPLICATIONS

This application is a continuation of U.S. application Ser. No. 17/939,060, which was filed on Sep. 7, 2022, which is a continuation of U.S. application Ser. No. 16/527,613, which was filed Jul. 31, 2019, now U.S. Pat. No. 11,468,320. The entire disclosure of both applications is incorporated herein by reference.

FIELD

The present disclosure relates generally to the technical field of machine learning. In a specific example, the present disclosure may relate to predicting drug directions of a prescription.

BACKGROUND

Doctors commonly use inconsistent language when describing instructions to a patient as to how to administer a prescription (i.e., prescription directions, often abbreviated "Signa" or Sig."). For example, directions to inject forty milligrams of a drug under the patient's skin every other week may be provided as one of the following variations: "INJECT 40 MG UNDER THE SKIN EVERY OTHER WEEK," "INJECT 40 MG UNDER THE SKIN EVERY OTHER WEEK AS DIRECTED," or "INJECT 40 MG UNDER THE SKIN EVERY OTHER WEEK (MAINTENANCE DOSE)." When the prescription is received by a pharmacy, a pharmacy technician must manually review and interpret the inconsistent language of the prescription directions before entering prescription data into a computer. This data entry process takes a significant amount of time and leads to inefficiencies. As such, there is a continuing need to remove these inefficiencies from a prescription filling process. For example, the present invention seeks to mitigate these inefficiencies by a computer predicting prescription drug directions using machine learning algorithms and displaying predictions to a pharmacy technician or automatically filling data values.

DETAILED DESCRIPTION

Figure 1:
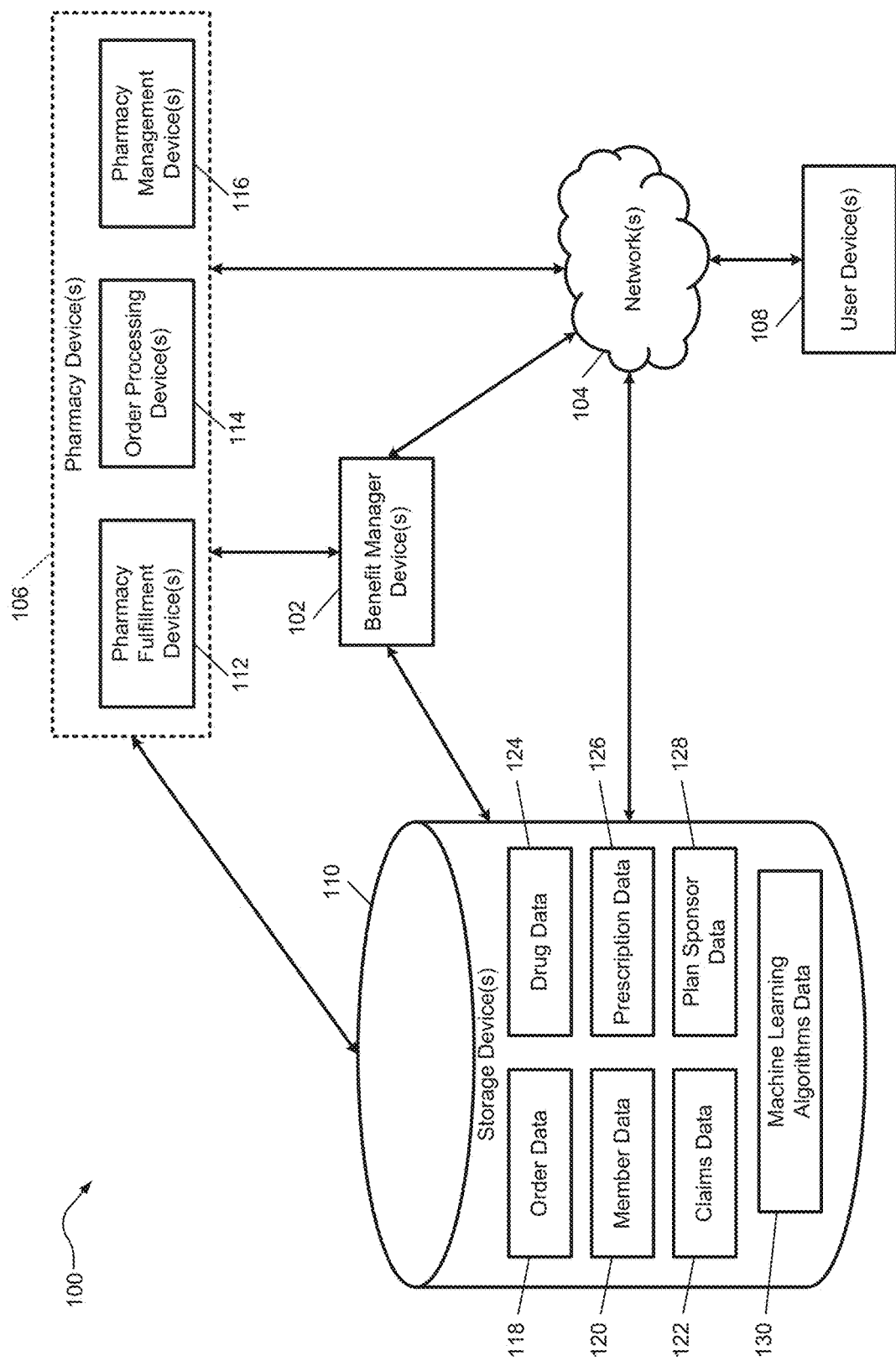
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

In some embodiments, the benefit manager device 102 can include a server, supercomputer, or other computing device configured to implement artificial intelligence algorithms, such as Neural Network, Random Forest, K-Neighbor, Gaussian Naïve Bayes, or Stochastic Gradient Descent ("SGD"). In some embodiments, the benefit manager device 102 can include a group of computers, such as an artificial neural network configured to implement artificial intelligence machine learning algorithms.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. In an example embodiment, a doctor or an assistant on behalf of the doctor can upload a prescription to the PBM (e.g. by transmitting a facsimile communication over the network 104). A technician can enter information related to the prescription into the pharmacy device 106 or request the benefit manager device 102 or the pharmacy device 106 to predict some or all values of required pharmacy elements (RPEs) related to the prescription using one of multiple machine learning algorithms. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device 108, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some embodiments, the order processing device 114 can include a server, supercomputer, or other computing device configured to implement artificial intelligence algorithms, such as Neural Network, Random Forest, K-Neighbor, Gaussian Naïve Bayes, or Stochastic Gradient Descent ("SGD"). In some embodiments, the order processing device 114 can include a group of computers, such as an artificial neural network configured to implement artificial intelligence machine learning algorithms.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, plan sponsor data 128, and/or machine learning algorithm data 130. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Furthermore, the machine learning algorithms data 130 can include code or instructions necessary to implement each of multiple machine learning algorithms. The code or instructions can be implemented by one or more processors of the benefit manager device 102 or the pharmacy device 106 (e.g., order processing device(s) 114, etc.). Each of the multiple machine learning algorithms can make a prediction for a particular prescription (e.g. a prescription received via fax) based on one or more predetermined factors (e.g. patient age, patient gender, prescribed drug, patient medical conditions), a prediction process that can be performed each time a faxed prescription is received. Each of the multiple machine learning algorithms can include code or instructions to learn from a training dataset, as would be understood by one having ordinary skill in the art. Each of the multiple algorithms can change or adapt the code or instructions based on learning from the training dataset and make predictions according to the changed code or instructions. According to an exemplary embodiment, the multiple machine learning algorithms can include one or more neural network machine learning algorithms. According to alternative exemplary embodiments, the multiple machine learning algorithms can include the Random Forest machine learning algorithm, the K-Neighbor machine learning algorithm, the Gaussian Naïve Bayes machine learning algorithm, and the SGD machine learning algorithm. In addition, each of the multiple machine learning algorithms can generate confidence values when making a prediction. According to an exemplary embodiment, a confidence value can be a statistical value generated by running statistical analysis on the predictions, and the confidence level can be used to gauge how likely the predictions are to being accurate.

In some embodiments, each of the multiple machine learning algorithms can make a prediction as to drug directions for taking or administering the prescription. By predicting the drug directions, each of the machine learning algorithms can display the predicted directions and/or auto-populate values in a prescription form with the predicted values, thereby saving time for a pharmacist or a pharmacist technician in filling a prescription Each of the multiple machine learning algorithms can make predictions as to drug directions for a prescription using predetermined factors, such as patient age, patient gender, which drug has been prescribed, and medical conditions. Different factors can be used to make drug direction predictions, and the factors and number of factors used to make drug direction predictions can depend on which predetermined factors best lead to prediction accuracy. Each of the multiple machine learning algorithms can learn and improve prediction success using a training dataset by factoring all or some of the predetermined factors listed above. Furthermore, after learning from the training dataset, each of the multiple machine learning algorithms can make drug direction predictions for a particular prescription based on all or some of the factors.

Figure 2:
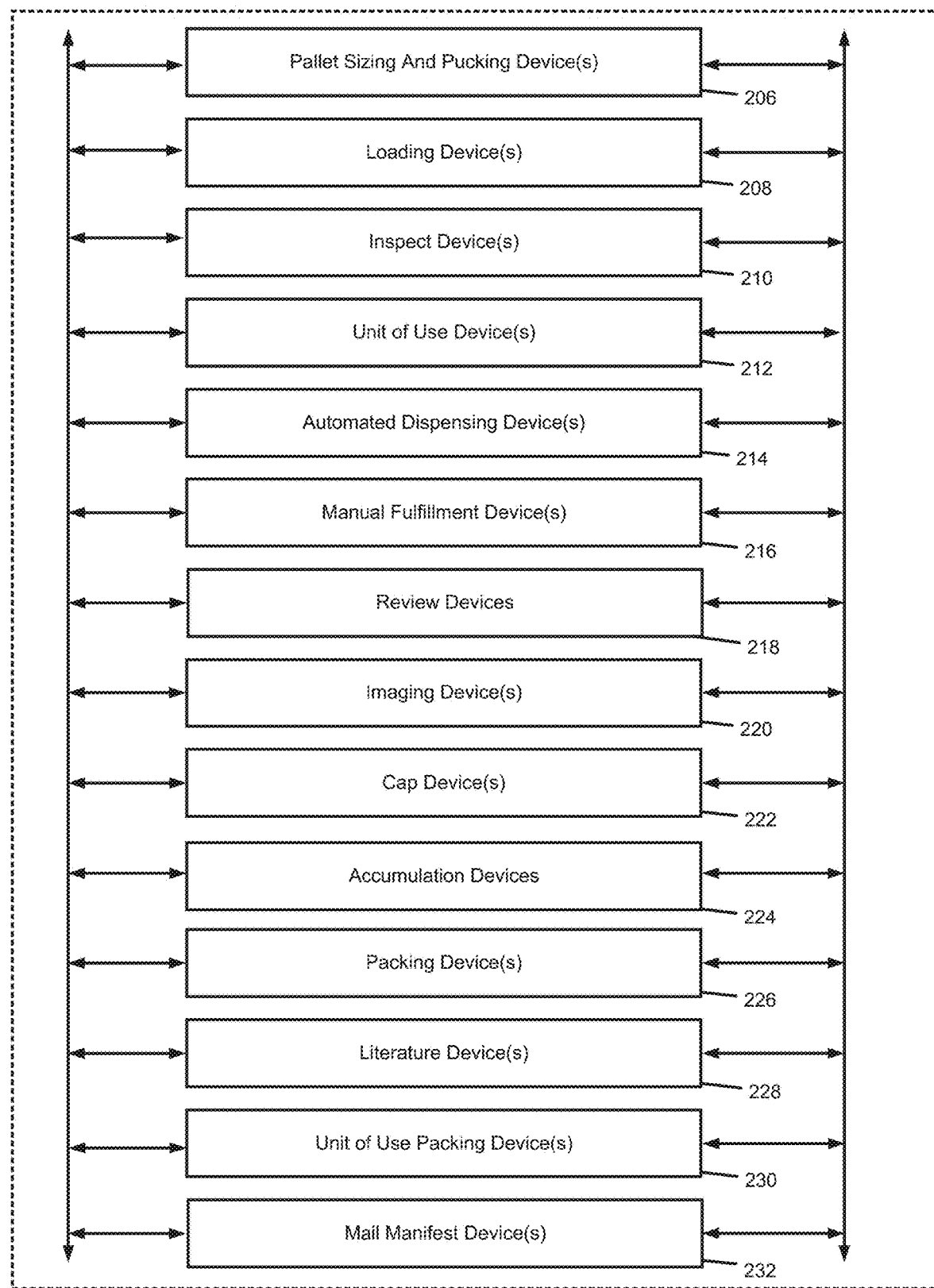
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
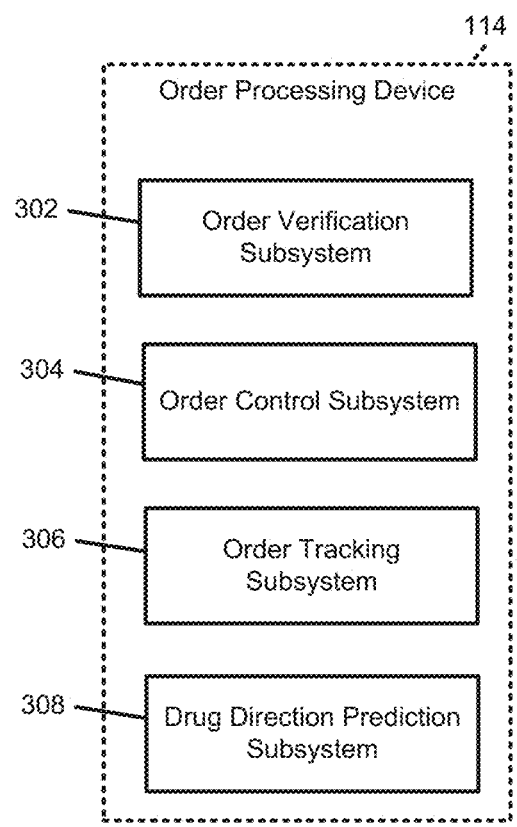
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order related components.

The order processing device 114 may receive instructions to fulfill an order without operator intervention. An order component may include a prescription drug fulfilled by use of a container through the system 100. The order processing device 114 may include an order verification subsystem 302, an order control subsystem 304, an order tracking subsystem 306, and/or a drug direction prediction subsystem 308. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

According to an exemplary embodiment, the drug direction prediction subsystem 308 can predict prescription drug directions from required pharmacy element values and directions in a prescription. The drug direction prediction subsystem 308 can periodically train and update the machine learning algorithms. For example, every Sunday evening, the drug direction prediction subsystem 308 can gather records involving prescription claims; however, the drug direction prediction subsystem 308 can perform data gathering other days or times (e.g. once a month on the first of the month, once a day at midnight, etc.).

After gathering the records, the drug direction prediction subsystem 308 can select a first of the multiple machine learning algorithms and train the first of the multiple machine learning algorithms using a predetermined percentage of the gathered records (e.g. 80% of the records). According to an exemplary embodiment, training the first of the multiple machine learning algorithms can include the first of the multiple machine learning algorithms analyzing each record to determine the known RPE values and a relationship between the known RPE values and drug directions. However, training the first of the multiple machine learning algorithms can include additional processes.

After training, the drug direction prediction subsystem 308 can implement the first of the multiple machine learning algorithms, as trained, on the remainder of the gathered records (e.g. the remaining 20% of the records) to determine a success rate of the first of the multiple machine learning algorithms at predicting drug directions for the remainder of the gathered records. The success rate can be a percentage value indicating how often the first of the multiple machine learning algorithms correctly predicted drug directions for an individual prescription of the remainder of the gathered records.

The drug direction prediction subsystem 308 can repeat the process described above using a second of the multiple machine learning algorithms, namely the drug direction prediction subsystem 308 can train the second of the multiple machine learning algorithms using the predetermined percentage of the gathered records, the drug direction prediction subsystem 308 can implement the second of the multiple machine learning algorithms to predict drug directions on the remainder of the gathered records, and the drug direction prediction subsystem 308 can determine the success rate of the second of the multiple machine learning algorithms. This process repeats until the drug direction prediction subsystem 308 determines the success rate for each of the multiple machine learning algorithms. Finally, the machine learning algorithm having the highest success rate is chosen and utilized by the drug direction prediction subsystem 308.

In some embodiments, the drug direction prediction subsystem 308 can only make predictions when a confidence value is above a threshold (e.g. 80%, 90%, etc.). In addition, the drug direction prediction subsystem 308 may only auto-populate predictions having a confidence value over the threshold. Furthermore, predictions having a confidence value below the threshold can be excluded in calculating the success rate, or a prediction having a confidence level below the threshold can be counted as a failure in calculating the success rate.

The process of selecting a machine learning algorithm can repeat periodically (e.g. once a week) using the original dataset and any new data generated between a first iteration of the machine learning algorithms selection process and a second iteration of the machine learning algorithm selection process. For example, the first iteration may use three years of prescription data, and the second iteration may use three years and one week of prescription data, if the machine learning selection process is performed weekly.

Figure 4:
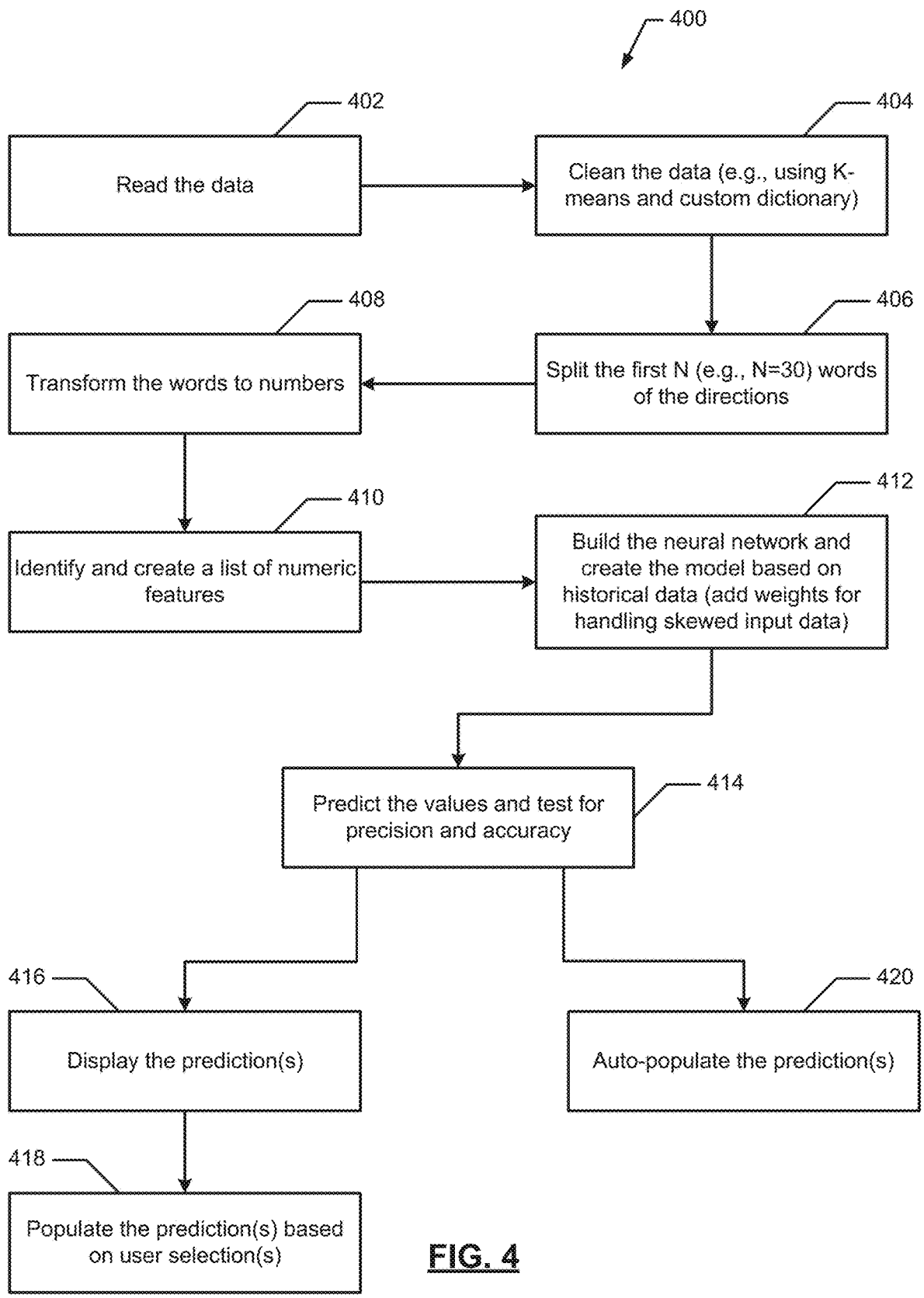
FIG. 4 is a block diagram of a flowchart illustrating methods for predicting prescription drug directions using machine learning algorithms, according to an example embodiment.

FIG. 4 illustrates a method 400 for predicting prescription drug directions using machine learning algorithms and displaying predictions to a pharmacy technician or automatically filling data values according to an example embodiment. The method 400 may be performed by the order processing device 114, partially by the order processing device 114 and partially by another device of the system 100, or may be otherwise performed. For the sake of simplicity, the order processing device 114 will be described as performing the steps of the method 400, but the embodiments described herein are not so limited.

According to an exemplary embodiment, the order processing device 114 can read patient prescription data in step 402. In some embodiments, the patient prescription data read in step 402 can include patient prescription data associated with one or more prescriptions received through facsimile, entered into a computer, and stored in a database. In some embodiment, the order processing device 114 can receive patient prescription data from the database.

Subsequently, for each prescription having associated patient prescription data stored in the database, the order processing device 114 can clean the patient prescription data in step 404. In some embodiments, the order processing device 114 can clean the data using k-means clustering and a custom dictionary. For example, the custom dictionary may standardize elements of the patient directions (e.g., fourteen days is equivalent to two weeks, etc.). Building and using the custom dictionary is described in greater detail below with regard to FIG. 5. As a result of step 404, the order processing device 114 can output a cleaned set of data used for future processing.

In step 406, for each prescription having associated patient prescription data stored in the database, the order processing device 114 can tokenize the directions associated with a respective prescription by splitting the directions into a predetermined number of words (e.g., N words). A token is an instance of a sequence of characters in the directions that are grouped together as a useful semantic for processing. In some embodiments, the tokenizing process groups characters together to determine words. In some embodiments, the order processing device 114 tokenizes the directions by distinguishing between the words of the directions based on whitespace between characters, abbreviations, and/or sentence breaks. Starting with the first character in the directions, the order processing device 114 can move along the characters in the directions and group them together until encountering a whitespace. Upon encountering the whitespace, the order processing device 114 sets the grouped characters as the first token (i.e., the first word) and then repeats the process until the predetermined number of words is reached. In some embodiments, the predetermined number of words can be thirty, and the order processing device 114 can split the directions into thirty words.

In step 408, for each prescription having associated patient prescription data stored in the database, the order processing device 114 can transform the words or tokens into numbers as part of a text vectorization process. For example, the order processing device 114 can make a dictionary (e.g., a vocabulary list) of unique words in the directions and then represent each sentence of the directions as a real valued vector with each word represented as 1 for present and 0 for absent from the dictionary (e.g., a "Bag of Words" approach). In some embodiments, the order processing device 114 can represent the words as a count of the number of times each word appears in the directions (e.g., a term frequency approach).

In step 410, the order processing device 114 can identify and create a list of numeric features based on transforming the words or tokens into the numbers as part of the text vectorization process. Step 410 is described in more detail below with reference to FIG. 6. In some embodiments, steps 404 through 410 can be referred to as pre-processing the patient prescription data. Furthermore, steps 404-410 can repeat for each prescription having associated patient prescription data stored the database. Alternatively, the order processing device 114 can perform steps 404-410 on a subset of the prescriptions having patient prescription data stored in the database (e.g. 80% of the prescriptions).

In step 412, the order processing device 114 can build an artificial neural network model based on historical data and based on the pre-processing of the patient prescription data in steps 402-410. An example artificial neural network model is described in more detail below with reference to FIG. 7.

In step 414, the order processing device 114 can receive a new prescription and can make a prediction regarding prescription drug directions included within the new prescription using machine learning algorithms. In addition, the order processing device 114 can test the predictions for precision and accuracy.

In step 416, the order processing device 114 can display the predicted prescription drug directions to a user, who may be a pharmacist or pharmacist technician, for example. In some embodiments, the predicted prescription drug directions can be displayed on a graphical user interface on a computer. In step 418, the order processing device 114 can populate predicted prescription drug directions in a prescription form based on user selections of the displayed predicted prescription drug directions, thereby saving time for a pharmacist or pharmacist technician in filling a prescription.

Alternatively, in step 420, the order processing device 114 can auto-populate predicted prescription drug directions in the prescription form, thereby saving time for a pharmacist or pharmacist technician in filling a prescription.

Figure 5:
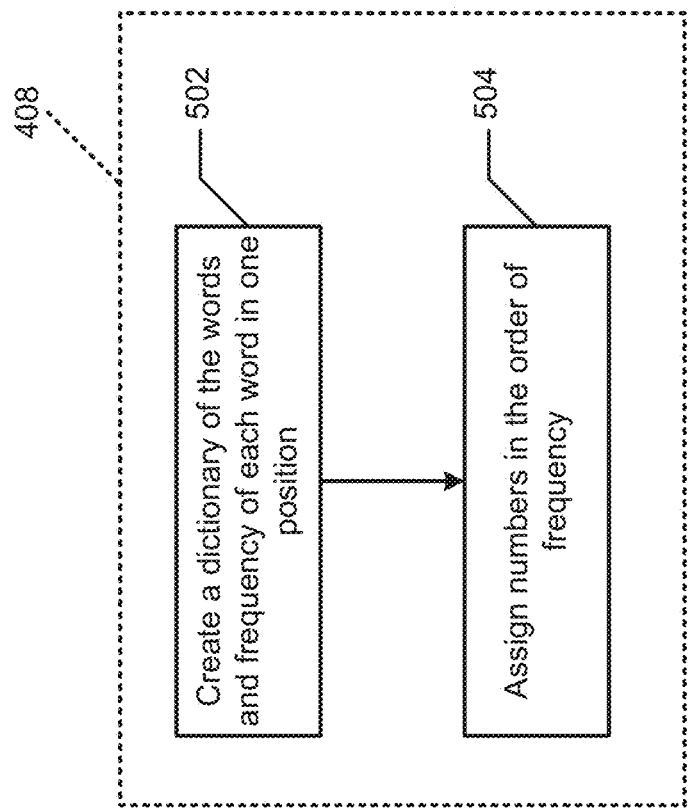
FIG. 5 is a block diagram of a flowchart illustrating methods for transforming words in prescription drug directions to numbers for processing by machine learning algorithms, according to an example embodiment.

FIG. 5 illustrates a method for transforming words into numbers according to an example embodiment. In an embodiment, the illustrated method for transforming words into numbers forms, at least in part, step 408 of the method 400.

In step 502, the order processing device 114 can create a dictionary of the words and a frequency of each word in each position. For example, a dictionary of the words and frequencies may review, for example, 1033 distinct prescriptions, and as a result, the dictionary of the words and frequencies may include data indicating that a first word in the directions is "Inject" at a frequency of 573 prescriptions out of the 1033 prescriptions, that the first word in the directions is "Take" at a frequency of 337 prescriptions out of the 1033 prescriptions, and that the first word in the directions is "Use" at a frequency of 123 prescriptions out of the 1033 prescriptions. The dictionary can include words and frequencies for each subsequent word in the directions as well (e.g. the second word in the directions, the third word in the directions . . . the thirtieth word in the directions). The dictionary can also include data indicative of the words and frequencies up to the predetermined number (N) of the words in the directions.

In step 504, the order processing device 114 can assign a ranking that orders the frequencies. For example, ranking the frequencies may include "Inject=1, Take=2, Use=3" to indicate that "Inject" is the most frequent first word of the directions, "Take" is the second-most frequent first word of the directions, and "Use" is the third-most frequent first word of the directions.

Figure 6:
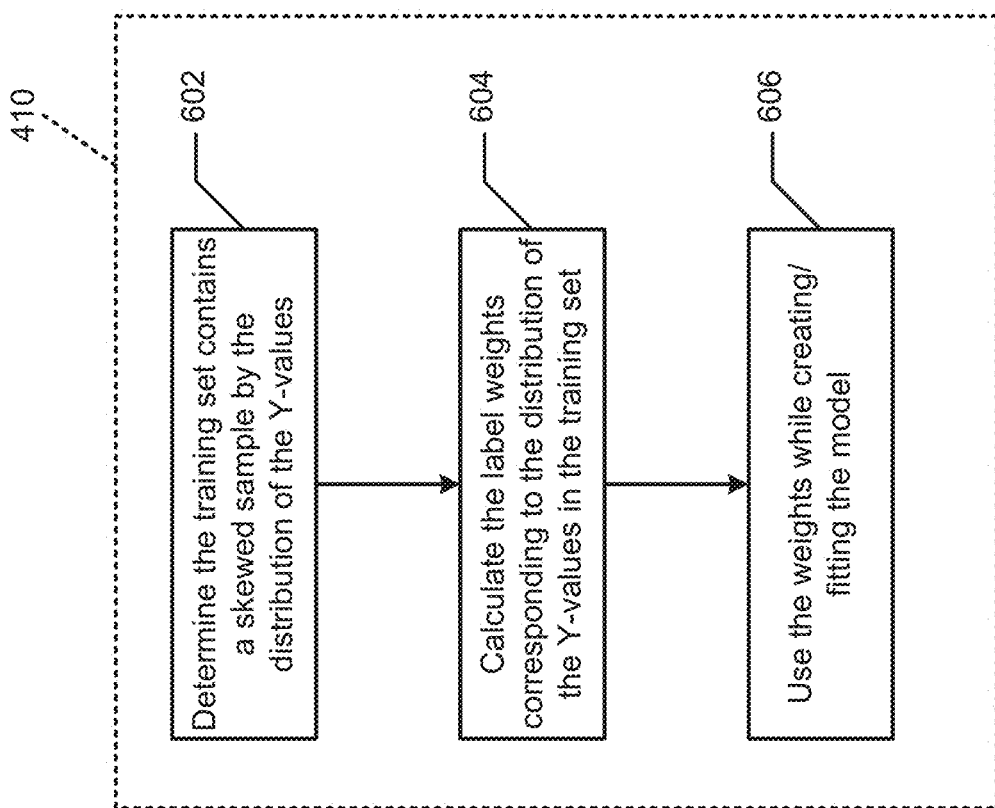
FIG. 6 is a block diagram of a flowchart illustrating methods for identifying and creating a list of numeric features in transformed words, according to an example embodiment.

FIG. 6 illustrates a method for identifying and creating a list of numeric features according to an example embodiment. In an embodiment, the illustrated method for identifying and creating a list of numeric features forms, at least in part, step 410 of the method 400.

In step 602, the order processing device 114 can determine that the training set contains a skewed sample by the distribution of the Y-values. In some embodiments, the order processing device 114 can determine the training set is skewed if one tail of the distribution is longer than the other (i.e., an asymmetrical distribution). For example, a left-skewed (i.e., negatively skewed) distribution has a long left tail and a right-skewed (i.e., positively skewed) distribution has a long right tail. In some embodiments, upon determining that the training set contains a skewed sample, the order processing device 114 can prevent skewed training data from being fed into the artificial neural network model. For example, if Category A of the training data includes 9000 training data points and Category B of the training data contains only 1000 training data points, then the artificial neural network model will be biased toward Category A. If this skewed training data were fed into the artificial neural network model, then the model would ignore Category B and instead predict the output as Category A, thus gaining pseudo-accuracy while losing precision. The order processing device 114 can prevent the skewed training data from being fed into the artificial neural network by, for example, weighting the skewed samples of the training data as described below.

In step 604, the order processing device 114 can calculate label weights corresponding to a distribution of Y-values in a training set. In an embodiment, the order processing device 114 can calculate the label weights for a category by dividing the total number of samples by the total number of samples in a category (i.e., weight for a category=total number of samples/total number of samples in the category). In an embodiment, the samples are derived from prior prescriptions and include the data coming in from prescribers (e.g., doctors, etc.) and the data approved by the pharmacist (or pharmacist technician). As the number of samples increases the label weight will decrease, and as the number of samples in a category decreases the label weight will increase. For example, a frequency distribution may be as follows: Type 0—10000, Type 1—3000, Type 2—500, Type 3—900. The label weight of Type 0 can be set to 1 (e.g., the maximum frequency of Type 0 with a frequency of 10000). The subsequent label weights for each type can be calculated by dividing the maximum frequency with the frequency of the type (i.e., label weight of Type N=max frequency/frequency of Type N). Accordingly, in this example the label weight of Type 1 is 3.33 (i.e., 10000/3000), the label weight of Type 2 is 20 (i.e., 10000/500), and the label weight of Type 3 is 11.11 (i.e., 10000/900). Accordingly, the final list of label weights to be applied to the skewed training data samples of this example embodiment will be [1, 3.33, 20, 11.11]. As will be understood by those of ordinary skill in the art, the label weights applied to skewed training data samples are different from the input value weights associated with the artificial neural network further described herein. The label weights are calculated by the order processing device 114 while training the artificial neural network model and label weights are calculated for each set of training data used for training the artificial neural network model.

In step 606, the order processing device 114 can use the label weights while creating and fitting the model.

Figure 7:
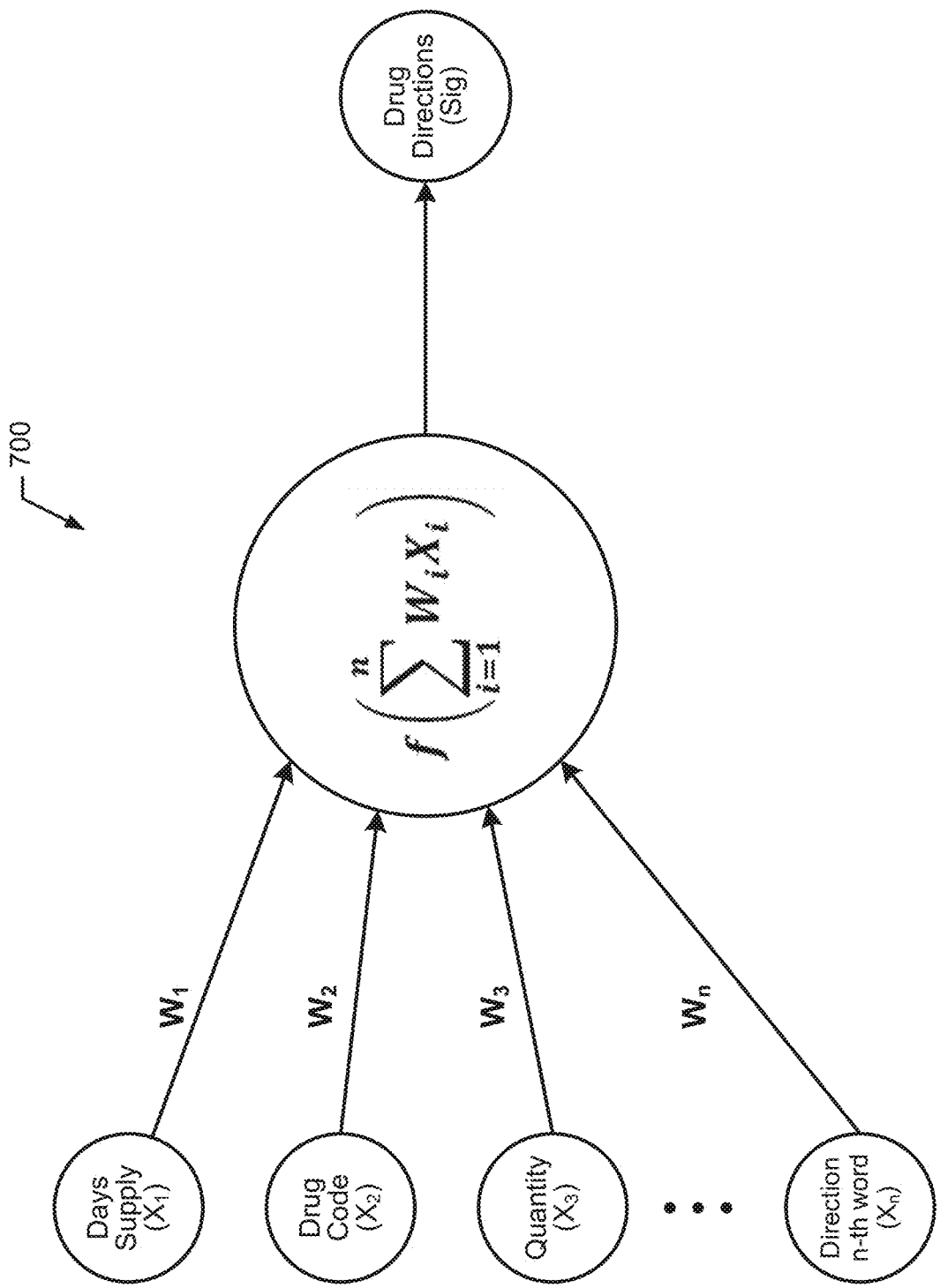
FIG. 7 is a diagram of an artificial neural network for predicting prescription drug directions from required pharmacy element values and directions in a prescription, according to an example embodiment.

FIG. 7 illustrates an artificial neural network 700 for predicting prescription drug directions from required pharmacy element values and directions in a prescription, according to an example embodiment. In an embodiment, required pharmacy element values and directions in a prescription, represented as X values in FIG. 7, are each inputted to the artificial neural network 700. For example, inputted required pharmacy elements may include days' supply ($X_1$), drug code (e.g., National Drug Code (NDC), etc.) ($X_2$), and quantity ($X_3$). Additional exemplary required pharmacy elements include, but are not limited to, a number of refills authorized by a doctor who prescribed the prescription, a price of the prescription, and a co-pay amount for the prescription. Each word of the prescription directions, up to the n-th word ($X_n$), may also be inputted to the artificial neural network 700. The inputted pharmacy element values and directions may each be weighted with a value (e.g., $W_1$, $W_2$, $W_3$, $W_n$, etc.) as further described herein. The artificial neural network 700 can predict and output the prescription drug directions by performing an activation function on the weighted input values. For example, the activation function illustrated in FIG. 7 is $$f\left(\sum_{i=1}^{n} W_i X_i\right).$$

Figure 8:
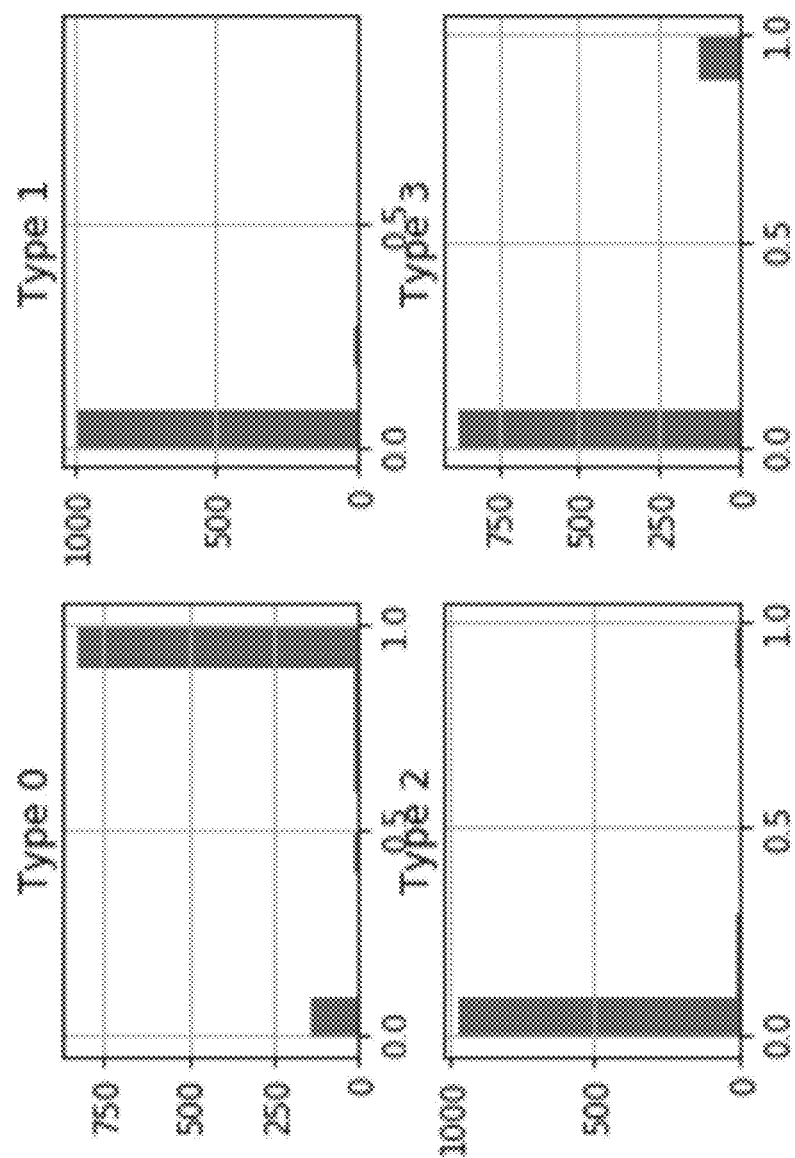
FIG. 8 is a diagram of confidence values for predicted prescription drug directions, according to an example embodiment.

For example, the days' supply input ($X_1$) may have a value of 28, the drug code input ($X_2$) may have a value of 00074433902, the quantity input ($X_3$) may have a value of 2, the direction first word input ($X_4$) may have a value of "take", the direction second word input ($X_5$) may have a value of "one", the direction third word input ($X_6$) may have a value of "every", the direction fourth word input ($X_7$) may have a value of "two", and the direction fifth word input ($X_8$) may have a value of "weeks". By performing the activation function illustrated in FIG. 7 on these inputs, the artificial neural network 700 can predict four types of prescription drug directions: "Type 0=INJECT 40 MG UNDER THE SKIN EVERY OTHER WEEK", "Type 1=INJECT 40 MG UNDER THE SKIN EVERY WEEK (MAINTENANCE DOES)", "Type 2=INJECT 40 MG UNDER THE SKIN EVERY OTHER WEEK AS DIRECTED", and "Type 3=INJECT 40 MG UNDER THE SKIN EVERY WEEK". FIG. 8 illustrates the confidence level of the four predicted types. In this example embodiment, artificial neural network 700 is most confident in Type 0 and thus outputs "INJECT 40 MG UNDER THE SKIN EVERY OTHER WEEK" as the predicted prescription drug direction. In other words, Type 0 has the highest confidence value of the four types and thus artificial neural network 700 selects Type 0 because it has the highest confidence value in this example embodiment.

In another example, the artificial neural network 700 may continually learn which particular input values are associated with particular directions. For example, the drug code input ($X_2$) may have a value that is indicative of a drug that is in the form of an orally administered pill. The artificial neural network 700 can understand that when the drug code input ($X_2$) has that value indicative of a drug that is in the form of an orally administered pill then the chances of the drug directions including the word "inject" are low (e.g., near 0%) but the chances of the drug directions including the word "orally" are high (e.g., near 100%). In this example embodiment, the artificial neural network 700 may assign a large weight value ($W_2$) to the drug code input ($X_2$) because the drug code value has a high correlation to the drug direction confidence level. But the artificial neural network 700 may be capable of continually learning which input values have high correlations to the drug direction confidence level and re-assigning the weight values accordingly. For instance, the artificial neural network 700 may learn that a different input value, or certain combination of input values, has a higher correlation to the drug direction confidence level than the drug code input ($X_2$) alone. In such an instance, the artificial neural network 700 may update the weighting values to implement the updated information about the correlation between the input values and the drug direction confidence level.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Example methods and systems for using machine learning algorithms are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

What is claimed is:
1. A system for automatically processing prescriptions, the system comprising:
   a memory component, configured to store a plurality of prescriptions;
   at least one processor communicatively coupled to the memory component, the at least one processor configured to:

receive and pre-process values of a plurality of required pharmacy elements for a corresponding prescription of the plurality of prescriptions;

generate respective weights for the values of the plurality of required pharmacy elements of the prescription based on one or more of the values of the plurality required pharmacy elements of the prescription;

create a machine learning model to be used by the applicable one of the plurality of machine learning algorithms in predicting drug directions of the prescription, the machine learning model using the values of the plurality of required pharmacy elements of the prescription and the respective weights; and predict a plurality of drug directions of a new prescription by executing the machine learning model using weighted values of the plurality of required pharmacy elements of the new prescription.

2. The system of claim 1, wherein the at least one processor is further configured to:

obtain records, to create obtained records;

train a first one of a plurality of machine learning algorithms stored in the memory component using a predetermined percentage of the obtained records, to create a trained first algorithm, wherein the obtained records include the predetermined percentage and a remainder;

implement the trained first algorithm on the remainder of the obtained records;

determine a first success rate of the trained first algorithm, based on implementing the trained first algorithm on the remainder;

train a second one of the plurality of machine learning algorithms stored in the memory component using the predetermined percentage of the obtained records, to create a trained second algorithm;

implement the trained second algorithm on the remainder of the obtained records;

determine a second success rate of the trained second algorithm;

perform a comparison of the first success rate and the second success rate; and select either the trained first algorithm or the trained second algorithm based on the comparison.

3. The system of claim 2, wherein the at least one processor trains the first one of the plurality of machine learning algorithms by being further configured to:

use the first one of the plurality of machine learning algorithms to perform an analysis of each of the predetermined percentage of the obtained records; and determine known values for required pharmacy elements and relationships between the known values and drug directions for the predetermined percentage, based on the analysis.

4. The system of claim 2, wherein the first success rate indicates a frequency of the first trained algorithm correctly predicting drug directions for an individual prescription of the remainder of the obtained records.

5. The system of claim 2, wherein the at least one processor is further configured to:

identify a highest success rate, based on the comparison of the first success rate and the second success rate; and use the highest success rate to select either the trained first algorithm or the trained second algorithm.

6. The system of claim 1, wherein the at least one processor tests the machine learning model using current data, by being further configured to:

determine a success rate associated with the machine learning model.

7. The system of claim 1, wherein the at least one processor is further configured to:

test the machine learning model according to a timed interval schedule; and determine whether to replace or retrain the machine learning module on an ongoing basis, according to the timed interval schedule.

8. The system of claim 1, wherein the plurality of machine learning algorithms comprise neural network machine learning algorithms.

9. A method comprising:

a drug direction prediction subsystem receiving and pre-processing values of a plurality of required pharmacy elements for a corresponding prescription of a plurality of prescriptions;

the drug direction prediction subsystem generating respective weights for the values of the plurality of required pharmacy elements of the prescription based on one or more of the values of the plurality required pharmacy elements of the prescription;

the drug direction prediction subsystem creating a machine learning model to be used by the applicable one of the plurality of machine learning algorithms in predicting drug directions of the prescription, the machine learning model using the values of the plurality of required pharmacy elements of the prescription and the respective weights; and the drug direction prediction subsystem predicting a plurality of drug directions of a new prescription by executing the machine learning model using weighted values of the plurality of required pharmacy elements of the new prescription.

10. The method of claim 9, further comprising:

obtaining records, to create obtained records;

training a first one of a plurality of machine learning algorithms stored in the memory component using a predetermined percentage of the obtained records, to create a trained first algorithm, wherein the obtained records include the predetermined percentage and a remainder;

implementing the trained first algorithm on the remainder of the obtained records;

determining a first success rate of the trained first algorithm, based on implementing the trained first algorithm on the remainder;

training a second one of the plurality of machine learning algorithms stored in the memory component using the predetermined percentage of the obtained records, to create a trained second algorithm;

implementing the trained second algorithm on the remainder of the obtained records;

determining a second success rate of the trained second algorithm;

performing a comparison of the first success rate and the second success rate; and select either the trained first algorithm or the trained second algorithm based on the comparison.

11. The method of claim 10, wherein training the first one of the plurality of machine learning algorithms further comprises:

using the first one of the plurality of machine learning algorithms to perform an analysis of each of the predetermined percentage of the obtained records; and determining known values for required pharmacy elements and relationships between the known values and drug directions for the predetermined percentage, based on the analysis.

12. The method of claim 10, wherein the first success rate indicates a frequency of the first trained algorithm correctly predicting drug directions for an individual prescription of the remainder of the obtained records.

13. The method of claim 10, further comprising:
identifying a highest success rate, based on the comparison of the first success rate and the second success rate; and
using the highest success rate to select either the trained first algorithm or the trained second algorithm.

14. The method of claim 9, wherein testing the subset of the plurality of machine learning algorithms using current data and previously obtained data, further comprises:
determining a success rate associated with the machine learning model.

15. The method of claim 9, further comprising:
testing the machine learning model according to a timed interval schedule; and
determining whether to replace or retrain the machine learning module on an ongoing basis, according to the timed interval schedule.

16. The method of claim 9, wherein the plurality of machine learning algorithms comprise neural network machine learning algorithms.

17. The method of claim 9, further comprising:
displaying the plurality of predicted drug directions of the new prescription;
receiving a user selection of one of the plurality of displayed predicted drug directions, to create a selected drug direction; and
populating a form with the selected drug direction.

18. A non-transitory machine-readable medium comprising instructions, which, when executed by one or more processors, cause the one or more processors to perform the following operations:
receive and pre-process values of a plurality of required pharmacy elements for a corresponding prescription of the plurality of prescriptions;
generate respective weights for the values of the plurality of required pharmacy elements of the prescription based on one or more of the values of the plurality required pharmacy elements of the prescription;
create a machine learning model to be used by the applicable one of the plurality of machine learning algorithms in predicting drug directions of the prescription, the machine learning model using the values of the plurality of required pharmacy elements of the prescription and the respective weights; and
predict a plurality of drug directions of a new prescription by executing the machine learning model using weighted values of the plurality of required pharmacy elements of the new prescription.

19. The non-transitory, computer-readable medium of claim 18, further causes the one or more processors to perform the following operations:
obtain records, to create obtained records;
train a first one of a plurality of machine learning algorithms stored in the memory component using a predetermined percentage of the obtained records, to create a trained first algorithm, wherein the obtained records include the predetermined percentage and a remainder;
implement the trained first algorithm on the remainder of the obtained records;
determine a first success rate of the trained first algorithm, based on implementing the trained first algorithm on the remainder;
train a second one of the plurality of machine learning algorithms stored in the memory component using the predetermined percentage of the obtained records, to create a trained second algorithm;
implement the trained second algorithm on the remainder of the obtained records;
determine a second success rate of the trained second algorithm;
perform a comparison of the first success rate and the second success rate; and
select either the trained first algorithm or the trained second algorithm based on the comparison.

20. The non-transitory, computer-readable medium of claim 19, further causes the one or more processors to perform the following operations:
use the first one of the plurality of machine learning algorithms to perform an analysis of each of the predetermined percentage of the obtained records; and
determine known values for required pharmacy elements and relationships between the known values and drug directions for the predetermined percentage, based on the analysis.

* * * * *